(12) United States Patent
Hakamada et al.

(10) Patent No.: US 7,033,981 B2
(45) Date of Patent: Apr. 25, 2006

(54) ALKALINE CELLULASE VARIANTS

(75) Inventors: Yoshihiro Hakamada, Tochigi (JP); Kazuhisa Sawada, Tochigi (JP); Keiji Endo, Tochigi (JP); Hiroshi Kodama, Tochigi (JP); Yasunao Wada, Wakayama (JP); Shitsu Shikata, Wakayama (JP); Tohru Kobayashi, Tochigi (JP)

(73) Assignee: Kao Corporation, Tokyo (JP)

( * ) Notice: Subject to any disclaimer, the term of this patent is extended or adjusted under 35 U.S.C. 154(b) by 371 days.

(21) Appl. No.: 10/383,630

(22) Filed: Mar. 10, 2003

(65) Prior Publication Data

US 2004/0002431 A1 Jan. 1, 2004

(30) Foreign Application Priority Data

Mar. 27, 2002 (JP) .............................. 2002-089531
Jan. 22, 2003 (JP) .............................. 2003-013840

(51) Int. Cl.
*C11D 3/386* (2006.01)
*C12N 9/42* (2006.01)
*C12N 1/20* (2006.01)
*C12N 15/00* (2006.01)
*C07H 21/04* (2006.01)

(52) U.S. Cl. .................... 510/226; 435/209; 435/252.3; 435/320.1; 510/320; 536/23.2

(58) Field of Classification Search ................ 510/226, 510/320; 435/209, 252.3, 320.1; 536/23.2
See application file for complete search history.

(56) References Cited

U.S. PATENT DOCUMENTS 4,945,053 A 7/1990 Ito et al. ...................... 435/209

FOREIGN PATENT DOCUMENTS

| JP | 50-28515 | 9/1975 |
|---|---|---|
| JP | 60-23158 | 6/1985 |
| JP | 6-30578 | 4/1994 |
| JP | 10-313859 | 12/1998 |
| JP | 2000-210081 | 8/2000 |
| WO | WO 98/12307 | 3/1998 |

OTHER PUBLICATIONS

Accession No. AAR26021 (see the enclosed sequence search alignment between Applicants' SEQ ID No.: 2 and Accession No. AAR26021, and notes therein).*
Derwent Abstracts, Database Geneseq Online !, Database Accession No. AAG80267, 1 page, XP-002251476, JP 2001-231569, Aug. 28, 2001.
Derwent Abstracts, Database Genesq Online !, Database Accession No. AAR26021, 1 page, XP-002251477, JP 04-190793, Jul. 9, 1992.
K. Horikoshi, et al., Alkalophilic Microorganisms, pp. 126-129, "Enzymes of Alkalophilic Bacteria", 1982.
Derwent Abstracts, Database Geneseq Online !, Database Accession No. AAG80267, 1 page, XP-002251476, JP 2001-231569, Aug. 28, 2001.
Derwent Abstracts, Database Geneseq Online 1, Database Accesion No. AAR26021, 1 page, XP-002251477, JP 04-190793, Jul. 9, 1992.

* cited by examiner

*Primary Examiner*—Tekchand Saidha
(74) *Attorney, Agent, or Firm*—Oblon, Spivak, McClelland, Maier & Neustadt, P.C.

(57) ABSTRACT

The present invention relates to alkaline cellulase variants having an amino acid sequence which exhibits at least 95% homology with the amino acid sequence of SEQ ID NO: 2, wherein said alkaline cellulase variant is mutated to include at least one substitution at (a) position 10, (b) position 16, (c) position 22, (d) position 33, (e) position 39, (f) position 76, (g) position 109, (h) position 242, (i) position 263, (j) position 308, (k) position 462, (l) position 466, (m) position 468, (n) position 552, (o) position 564, or (p) position 608 in SEQ ID NO: 2, or at a position corresponding thereto, wherein said alkaline cellulase variant has alkaline cellulase activity. The present invention also relates to a gene encoding the variant; a vector containing the gene; a transformant containing the vector; and a detergent composition containing the alkaline cellulase variant.

25 Claims, 1 Drawing Sheet

Fig. 1

SEQ ID NO: 1

```
            10   16    22     33  39                                            76
             ↓    ↓     ↓      ↓   ↓                                             ↓
Egl-237    1:MMLRKKTKQLISSILILVLLLSLFPAALAAEGNTREDNFKHLLGNDNVKRPSEAGALQLQEVDGQMTLVDQHGEKIQLRGMSTHGLQWFP 90
Egl-1139   1:MMLRKKTKQLISSILILVLLLSLFPTALAAEGNTREDNFKHLLGNDNVKRPSEAGALQLQEVDGQMTLVDQHGEKIQLRGMSTHGLQWFP 90
Egl-64     1:MMLRKKTKQLISSILILVLLLSLFPTALAAEGNTREDNFKHLLGNDNVKRPSEAGALQLQEVDGQMTLVDQHGEKIQLRGMSTHGLQWFP 90
Egl-N131b  1:MMLRKKTKQLGR-----------PAQA--EGNTREDNFKHLLGNDNVKRPSEAGALQLQEVDGQMTLVDQHGEKIQLRGMSTHGLQWFP 76
             ***********           ****  ******************************************************

109
                      ↓
Egl-237   91:EILNDNAYKALSNDWDSNMIRLAMYVGENGYATNPELIKQRVIDGIELAIENDMYVIVDWHVHAPGDPRDPVYAGAKDFFREIAALYPNN 180
Egl-1139  91:EILNDNAYKALANDWESNMIRLAMYVGENGYASNPELIKSRVIKGIDLAIENDMYVIVDWHVHAPGDPRDPVYAGAEDFFRDIAALYPNN 180
Egl-64    91:EILNDNAYKALANDWESNMIRLAMYVGENGYASNPELIKSRVIKGIDLAIENDMYVIVDWHVHAPGDPRDPVYAGAEDFFRDIAALYPNN 180
Egl-N131b 77:EILNDNAYKALSNDWDSNMIRLAMYVGENGHATNPELIKQRVIDGIELAIENDMYVIVDWHVHAPGDPRDPVYAGAKDFFREIAALYPNN 166
             ***********   ***************  ****** **** ** ****************************   *** *******

243         263
                                                                      ↓           ↓
Egl-237  181:PHIIYELANEPSSNNNGGAGIPNNEEGWKAVKEYADPIVEMLRKSGNADDNIIIVGSPNWSQRPDLAADNPIDDHHTMYTVHFYTGSHAA 270
Egl-1139 181:PHIIYELANEPSSNNNGGAGIPNNEEGWNAVKEYADPIVEMLRDSGNADDNIIVGSPNWSQRPDLAADNPIDDHHTMYTVHFYTGSHAA 270
Egl-64   181:PHIIYELANEPSSNNNGGAGIPNNEEGWNAVKEYADPIVEMLRDSGNADDNIIVGSPNWSQRPDLAADNPIDDHHTMYTVHFYTGSHAA 270
Egl-N131b167:PHIIYELANEPSSNNNGGAGIPNNEEGWKAVKEYADPIVQMLRKSGNADDNIIIVGSPNWSQRPDLAADNPIDDHHTMYTVHFYTGSHAA 256
             ****************************  ******** *** ****** ********************************

308
                              ↓
Egl-237  271:STESYPSETPNSERGNVMSNTRYALENGVAVFATEWGTSQASGDGGPYFDEADVWIEFLNENNISWANWSLTNKNEVSGAFTPFELGKSN 360
Egl-1139 271:STESYPPETPNSERGNVMSNTRYALENGVAVFATEWGTSQANGDGGPYFDEADVWIEFLNENNISWANWSLTNKNEVSGAFTPFELGKSN 360
Egl-64   271:STESYPPETPNSERGNVMSNTRYALENGVAVFATEWGTSQANGDGGPYFDEADVWIEFLNENNISWANWSLTNKNEVSGAFTPFELGKSN 360
Egl-N131b257:STESYPPETPNSERGNVMSNTRYALENGVAVFATEWGTSQANGDGGPYFDEADVWIEFLNENNISWANWSLTNKNEVSGAFTPFELGKSN 346
             ****** **********************************  *******************************************
```

(462)

```
Egl-237  361:ATNLDPGPDHVWAPEELSLSGEYVRARIKGVNYEPIDRTKYTKVLWDFNDGTKQGFGVNSDSPNKELIAVDNENNTLKVSGLDVSNDVSD 450
Egl-1139 361:ATSLDPGPDQVWVPEELSLSGEYVRARIKGVNYEPIDRTKYTKVLWDFNDGTKQGFGVNGDSPVEDVVIEN-EAGALKLSGLDASNDVSE 449
Egl-64   361:ATSLDPGPDQVWVPEELSLSGEYVRARIKGVNYEPIDRTKYTKVLWDFNDGTKQGFGVNGDSPVEDVVIEN-EAGALKLSGLDASNDVSE 449
Egl-N131b347:ATSLDPGPDQVWVPEELSLSGEYVRARIKGVNYEPIDRTKYTKVLWDFNDGTKQGFGVNSDSPNKELIAVDNENNTLKVSGLDVSNDVSD 436
             ** ****** ** ****************************************** *** *  **  *   *  **** *  ****
                     482 486 466
                      ↓   ↓  ↓
Egl-237  451:GNFWANARLSANGWGKSVDILGAEKLTMDVIVDEPTTVAIAAIPQSSKSGWANPERAVRVNAEDFVQQTDGKYKAGLTITGEDAPNLKNI 540
Egl-1139 450:GNYWANARLSADGWGKSVDILGAEKLTMDVIVDEPTTVSIAAIPQGPSANWVNPNRAIKVEPTNFVPLED-KFKAELTITSADSPSLEAI 538
Egl-64   450:GNYWANARLSADGWGKSVDILGAEKLTMDVIVDEPTTVSIAAIPQGPSANWVNPNRAIKVEPTNFVPLGD-KFKAELTITSADSPSLEAI 538
Egl-N131b437:GNFWANARLSANGWGKSVDILGAEKLTMDVIVDEPTTVAIAAIPQSSKSGWANPERAVRVNAEDFVQQTDGKYKAGLTITGEDAPSLEAI 526
             ** ******** **************************  **** *    ** * *  *  *** * *  **   ****  *  *   *
```

100% 
91.4% 
91.9% 
95.0%

```
                   552   564                                       698
                    ↓     ↓                                         ↓
Egl-237  541:AFHEEDNNMNNIILFVGTDAADVIYLDNIKVIGTEVEIPVVHDPKGEAVLPSVFEDGTRQGWDWAGESGVKTALTIEEANGSNALSWEFG 630
Egl-1139 539:AMHAENNNINNIILFVGTEGADVIYLDNIKVIGTEVEIPVVHDPKGEAVLPSVFEDGTRQGWDWAGESGVKTALTIEEANGSNALSWEFG 628
Egl-64   539:AMHAENNNINNIILFVGTEGADVIYLDNIKVIGTEVEIPVVHDPKGEAVLPSVFEDGTRQGWDWAGESGVKTALTIEEANGSNALSWEFG 628
Egl-N131b527:AMHAENYTINNIILFVGTEGADVIYLDTIKVIGTEVEIPVVHDPKGEAVLPSVFEDGTRQGWDWAGESGVKTALTIEEANGSNALSWEFG 616
             * * *    ***   ****  **********  *************************************************

Egl-237  631:YPEVKPSDNWATAPRLDFWKSDLVRGENDYVAPDFYLDPVRATEGAMNINLVPQPPTNGYWVQAPKTYTINFDELEEANQVNGLYHYEVK 720
Egl-1139 629:YPEVKPSDNWATAPRLDFWKSDLVRGENDYVTFDFYLDPVRATEGAMNINLVPQPPTNGYWVQAPKTYTINFDELEEPNQVNGLYHYEVK 718
Egl-64   629:YPEVKPSDNWATAPRLDFWKSDLVRGENDYVTFDFYLDPVRATEGAMNINLVPQPPTNGYWVQAPKTYTINFDELEEANQVNGLYHYEVK 718
Egl-N131b617:YPEVKPSDNWATAPRLDFWKSDLVRGENDYVTFDFYLDPVRATEGAMNINLVPQPPTNGYWVQAPKTYTINFDELEEANQVNGLYHYEVK 706
             ******************************  ********************************************** *********

Egl-237  721:INVRDITNIQDDTLLRNMMIIFADVESDFAGRVFVDNVRFEGAATTEPVEPEPVDPGEETPPVDEKEAKKEQKEAEKEEKEAVKEEKKEA 810
Egl-1139 719:INVRDITNIQDDTLLRNMMIIFADVESDFAGRVFVDNVRFEGAATTEPVEPEPVDPGEETPPVDEKEAKTEQKEAEKEEKEE-------- 800
Egl-64   719:INVRDITNIQDDTLLRNMMIIFADVESDFAGRVFVDNVRFEGAATTEPVEPEPVDPGEETPPVDEKEAKKEQKEAEKEEKEAVKEEKKEA 808
Egl-N131b707:INVRDITNIQDDTLLRNMMIIFADVESDFAGRVFVDNVRFEGAATTEPVEPEPVDPGEETPPVDEKEAKKEQKEAEKEEKEAVKEEKKEA 796
             ***************************************************************** ***********

Egl-237  811:KEEKKAVKNEAKKK                                                                           824
Egl-1139 801:--------------                                                                           801
Egl-64   809:KEEKKAIKNEATKK                                                                           822
Egl-N131b797:KEEKKAIKNEATKK                                                                           810
             ******  *** **
```

ALKALINE CELLULASE VARIANTS

TECHNICAL FIELD

The present invention relates to alkaline cellulase variants which can be incorporated in laundry detergents and the like.

BACKGROUND ART

Cellulases are enzymes which were considered to act only in a neutral or acid range but not in an alkaline laundry detergent solution. Finding of an alkaline cellulase derived from alkaliphilic microorganisms belonging to *Bacillus* sp. by Horikoshi (refer to Japanese Patent Publication No. Sho 50-28515 and Horikoshi & Akiba, Alkalophilic Microorganisms, Springer, Berlin, 1982) enabled its use for laundry heavy-duty detergents. Since then, alkaline cellulases produced by alkaliphilic microorganisms belonging to *Bacillus* sp. have been developed (refer to Japanese Patent Publication No. Sho 60-23158, Japanese Patent Publication No. Hei 6-030578 and U.S. Pat. No. 4,945,053) and are now incorporated in laundry detergents.

Recent progress in genetic engineering has enabled mass production of enzymes for detergents, which also applies to the production of alkaline cellulases. A number of genes for alkaline cellulases have already been cloned, their nucleotide sequences have been determined. Furthermore, technique for mutagenesis and breeding of the enzyme-producing bacteria or mutagenesis of a gene encoding the enzyme has been introduced.

Productivity of them on an industrial scale however does not reach a satisfactory level, and there is a demand for alkaline cellulases which can be produced efficiently.

An object of the present invention is therefore to provide an alkaline cellulase which acts favorably in an alkaline region, and can be mass produced readily because of having high secretion capacity or having enhanced specific activity.

DISCLOSURE OF THE INVENTION

The present inventors have searched a novel alkaline cellulase which can be produced efficiently without losing its inherent properties. As a result, it has been found that an alkaline cellulase variant, wherein an amino acid residue at a specific position of an amino acid sequence having at least 90% homology with the amino acid sequence represented by SEQ ID NO: 2 has been substituted with another amino acid residue, can be mass produced because it acquires high secretion capacity or enhanced specific activity.

In one aspect of the present invention, there are thus provided an alkaline cellulase variant obtained by substituting the amino acid residue of a cellulase having an amino acid sequence exhibiting at least 90% homology with the amino acid sequence represented by SEQ ID NO: 2 at (a) position 10, (b) position 16, (c) position 22, (d) position 33, (e) position 39, (f) position 76, (g) position 109, (h) position 242, (i) position 263, (j) position 308, (k) position 462, (l) position 466, (m) position 468, (n) position 552, (o) position 564, or (p) position 608 in SEQ ID NO: 2 or at a position corresponding thereto with another amino acid residue; and a gene encoding the alkaline cellulase variant.

In another aspect of the present invention, there are also provided a vector containing the gene and a transformant containing the vector.

In a further aspect of the present invention, there is also provided a detergent composition having the above-described alkaline cellulase variant incorporated therein.

BRIEF DESCRIPTION OF THE DRAWING

FIG. 1 shows aligned amino acid sequences of cellulases having at least 90% homology with the amino acid sequence represented by SEQ ID NO: 2.

BEST MODE FOR CARRYING OUT THE INVENTION

The alkaline cellulase variants according to the present invention are obtained by using, as a cellulase to be mutated (which may hereinafter be called "parent alkaline cellulase"), a cellulase having an amino acid sequence exhibiting at least 90% homology with the amino acid sequence represented by SEQ ID NO: 2 and replacing the amino acid residue of the parent alkaline cellulase at the position (a) to (p) in the above-described SEQ ID NO: 2 or at a position corresponding thereto with another amino acid residue. The alkaline cellulase variants may be wild-type variants or artificial variants.

Alkaline cellulases having an amino acid sequence exhibiting at least 90% homology with the amino acid sequence represented by SEQ ID NO: 2 and serving as a parent alkaline cellulase embrace alkaline cellulases having the amino acid sequence represented by SEQ ID NO: 2 and alkaline cellulases having an amino acid sequence exhibiting at least 90% homology with the above-described amino acid sequence. They may be either wild type alkaline cellulases or wild type variants. It is preferred that they have a molecular weight, as determined by the sodium dodecyl sulfate polyacrylamide gel electrophoresis (SDS-PAGE) or gel filtration, of 86,000±2,000; have the optimal pH value of 7.5 to 9.5 when carboxymethyl cellulose is used as a substrate; have the optimal temperature of 40 to 50° C.; favorably degrade lichenan in addition to carboxymethyl cellulose; and are sufficiently stable to incubation at pH 9 at 50° C. for 10 minutes. Particularly preferred are cellulases having a molecular weight of 86,000±2,000 (as determined by SDS-PAGE or gel filtration through a Sephacryl S200 column); having the optimum reaction pH of from 8.6 to 9.0; having the optimum reaction temperature of 50° C.; capable of favorably degrading lichenan as well as carboxymethyl cellulose; and being recognized to have residual activity of 95% or greater (assuming that the residual activity after treatment at 30° C. for 10 minutes is 100%) after treatment at 50° C. for 10 minutes at pH 9 in the presence of 5 mM calcium chloride.

Examples of the "alkaline cellulase having the amino acid sequence represented by SEQ. ID NO:1" include Eg1-237 [derived from *Bacillus* sp. strain KSM-S237 (FERM BP-7875), Hakamada, et al., Biosci. Biotechnol. Biochem., 64, 2281–2289, 2000]. Examples of the "alkaline cellulase having an amino acid sequence exhibiting at least 90% homology with the amino acid sequence represented by SEQ ID NO: 2" include alkaline cellulases having an amino acid sequence exhibiting preferably at least 95% homology, more preferably at least 98% homology, with the amino acid sequence represented by SEQ ID NO: 2. Specific examples include alkaline cellulase derived from *Bacillus* sp. strain 1139 (Eg1-1139) (Fukumori, et al., J. Gen. Microbiol., 132, 2329–2335) (91.4% homology), alkaline cellulases derived from *Bacillus* sp. strain KSM-64 (Eg1-64) (Sumitomo, et al., Biosci. Biotechnol. Biochem., 56, 872–877, 1992) (homology: 91.9%), and cellulase derived from *Bacillus* sp. strain KSM-N131 (Eg1-N131b) (Japanese Patent Application No. 2000-47237) (homology: 95.0%).

The homology of an amino acid sequence can be calculated using a program such as maximum matching or search homology of GENETYX-WIN (Software Development Co.).

The amino acid residues at positions (a) to (p) of the parent alkaline cellulase having the amino acid sequence represented by SEQ ID NO: 2 are (a) leucine at position 10, (b) isoleucine at position 16, (c) serine at position 22, (d) asparagine at position 33, (e) phenylalanine at position 39, (f) isoleucine at position 76, (g) methionine at position 109, (h) glutamine at position 242, (i) phenylalanine at position 263, (j) threonine at position 308, (k) asparagine at position 462, (l) lysine at position 466, (m) valine at position 468, (n) isoleucine at position 552, (o) isoleucine at position 564 and (p) serine at position 608.

In the parent alkaline cellulases having an amino acid sequence exhibiting at least 90% homology with the amino acid sequence represented by SEQ ID NO: 2, the amino acid residues at the positions corresponding to the above-described (a) to (p) of SEQ ID NO: 2 are preferably (a) leucine at position 10, (e) phenylalanine at position 39, (f) isoleucine at position 76, (h) glutamine at position 242, (i) phenylalanine at position 263, (k) asparagine at position 462, (l) lysine at position 466, (m) valine at position 468 and (n) isoleucine at position 552, of which the parent alkaline cellulase having, in addition to the above-described amino acid residues, (b) isoleucine at position 16 and (c) serine at position 22 are more preferred and that having, in addition to these residues, (d) asparagine at position 33, (g) methionine at position 109, (j) threonine at position 308, (o) isoleucine at position 564 and (p) serine at position 608 are still more preferred.

Accordingly, of the parent alkaline cellulases having an amino acid sequence exhibiting at least 90% homology with the amino acid sequence represented by SEQ ID NO: 2, preferred are cellulases having the above-described enzymatic properties and/or having an amino acid sequence exhibiting preferably at least 95%, more preferably at least 98% homology with the amino acid sequence represented by SEQ ID NO: 2, and moreover having, as amino acid residues at positions corresponding to the positions (a) to (p) of SEQ ID NO: 2, the above-described ones. Particularly preferred are cellulases having the above-described enzymatic properties, having an amino acid sequence exhibiting preferably at least 95%, more preferably at least 98% homology with the amino acid sequence represented by SEQ ID NO: 2, and moreover having, as amino acid residues at positions corresponding to the positions (a) to (p) of SEQ ID NO: 2, the above-described ones.

When a cellulase having the amino acid sequence represented by SEQ ID. NO: 2 is used as a parent alkaline cellulase, the alkaline cellulase variant of the present invention has an amino acid residue which is substituted for the amino acid residue at any one of the positions (a) to (p), while a cellulase having an amino acid sequence exhibiting at least 90% homology with the amino acid sequence represented by SEQ ID NO: 2 (except the alkaline cellulase represented by SEQ ID NO: 2) is used as a parent alkaline cellulase, the amino acid residue at a position corresponding to any one of the above-described positions (a) to (p) of SEQ ID NO: 2 has been substituted with another amino acid.

As such another amino acid residue, glutamine, alanine, proline or methionine, especially glutamine is preferred at position (a), asparagine or arginine, especially asparagine is preferred at position (b), proline is preferred at position (c), histidine is preferred at position (d), alanine, threonine or tyrosine, especially alanine is preferred at position (e), histidine, methionine, valine, threonine or alanine, especially histidine is preferred at position (f), isoleucine, leucine, serine or valine, especially isoleucine is preferred at position (g), alanine, phenylalanine, valine, serine, aspartic acid, glutamic acid, leucine, isoleucine, tyrosine, threonine, methionine or glycine, especially alanine, phenylalanine or serine is preferred at position (h), isoleucine, leucine, proline or valine, especially isoleucine is preferred at position (i), alanine, serine, glycine or valine, especially alanine is preferred at position (j), threonine, leucine, phenylalanine or arginine, especially threonine is preferred at position (k), leucine, alanine or serine, especially leucine is preferred at position (l), alanine, aspartic acid, glycine or lysine, especially alanine is preferred at position (m), methionine is preferred at position (n), valine, threonine or leucine, especially valine is preferred at position (o) and isoleucine or arginine, especially isoleucine is preferred at position (p).

The "amino acid residue at a position corresponding thereto" can be identified by comparing amino acid sequences by using known algorithm, for example, that of Lipman-Pearson's method, and giving a maximum similarity score to the multiple regions of similarity in the amino acid sequence of each alkaline cellulose. The position of the homologous amino acid residue in the sequence of each cellulase can be determined, irrespective of insertion or depletion existing in the amino acid sequence, by aligning the amino acid sequence of the cellulase in such manner (FIG. 1). It is presumed that the homologous position exists at the three-dimensional same position and it brings about similar effects with regard to a specific function of the target cellulase.

With regard to another alkaline cellulase having an amino acid sequence exhibiting at least 90% homology with SEQ ID NO: 2, specific examples of the positions corresponding to (a) position 10, (b), position 16, (c) position 22, (d) position 33, (e) position 39, (f) position 76, (g) position 109, (h) position 242, (i) position 263, (j) position 308, (k) position 462, (l) position 466, (m) position 468, (n) position 552, (o) position 564 and (p) position 608 of the alkaline cellulase (Eg1-237) represented by SEQ ID NO: 2 and amino acid residues at these positions will be shown below.

TABLE 1

|     | Egl-237 | Egl-1139 | Egl-64 | Egl-N131b |
| --- | --- | --- | --- | --- |
| (a) | 10Leu | 10Leu | 10Leu | 10Leu |
| (b) | 16Ile | 16Ile | 16Ile | Nothing corresponding thereto |
| (c) | 22Ser | 22Ser | 22Ser | Nothing corresponding thereto |
| (d) | 33Asn | 33Asn | 33Asn | 19Asn |
| (e) | 39Phe | 39Phe | 39Phe | 25Phe |
| (f) | 76Ile | 76Ile | 76Ile | 62Ile |
| (g) | 109Met | 109Met | 109Met | 95Met |
| (h) | 242Gln | 242Gln | 242Gln | 228Gln |
| (i) | 263Phe | 263Phe | 263Phe | 249Phe |
| (j) | 308Thr | 308Thr | 308Thr | 294Thr |
| (k) | 462Asn | 461Asn | 461Asn | 448Asn |
| (l) | 466Lys | 465Lys | 465Lys | 452Lys |
| (m) | 468Val | 467Val | 467Val | 454Val |
| (n) | 552Ile | 550Ile | 550Ile | 538Ile |
| (o) | 564Ile | 562Ile | 562Ile | 550Ile |
| (p) | 608Ser | 606Ser | 606Ser | 594Ser |

These amino acid residues may be substituted at two or more positions simultaneously as long as the substitution does not bring about any change in enzyme activity or enzymatic characteristics. Below-described are preferred specific examples of the case where substitution is carried out at two or more positions simultaneously. The amino acid is expressed by three letters, and "+" means that substitution at one position is followed by another substitution, while "/" means that any amino acid indicated thereby is usable.

Preferred double substitution examples include Leu10 (Gln/Ala/Pro/Met)+Ile16(Asn/Arg), Ile16(Asn/Arg)+Ser22Pro, Leu10(Gln/Ala/Pro/Met)+Ser22Pro, Asn33His+Phe39(Thr/Tyr/Ala), Leu10(Gln/Ala/Pro/Met)+Gln242(Ser/Ala/Phe/Val/Asp/Glu/Gly), Ile16(Arg/Asn)+Ser22Pro, Ser22Pro+Gln242(Ala/Ser/Phe/Val/Ile/Gly/Glu/Asp/Thr/Leu/Met/Tyr), Gln242(Ala/Ser/Phe/Val/Ile/Gly/Glu/Asp/Thr/Leu/Met/Tyr)+Phe263(Ile/Leu/Pro/Val), Leu10(Gln/Ala/Pro/Met)+Thr308(Ala/Ser/Gly/Val), Ile16(Asn/Arg)+Asn462(Thr/Leu/Phe/Arg), Ser22Pro+Val468(Ala/Asp/Gly/Lys), Asn33His+Ile552Met, Asn33His+Ile564(Val/Thr/Leu), and Gln242(Ala/Ser/Phe/Val/Ile/Gly/Glu/Asp/Thr/Leu/Met/Tyr)+Ser608(Ile/Arg), with Leu10Gln+Ser22Pro, Asn33His+Phe39Ala, Ser22Pro+Gln242Ala, Ser22Pro+Gln242Phe, and Ser22Pro+Gln242Ser being particularly preferred.

Preferred triple substitution examples include Leu10(Gln/Ala/Pro/Met)+Ser22Pro+Gln242(Ala/Ser/Phe/Val/Ile/Gly/Glu/Asp/Thr/Leu/Met/Tyr), Ile16(Asn/Arg)+Ser22Pro+Gln242(Ala/Ser/Phe/Val/Ile/Gly/Glu/Asp/Thr/Leu/Met/Tyr), and Ile76(His/Met/Val/Thr/Ala)+Gln242(Ala/Ser/Phe/Val/Ile/Gly/Glu/Asp/Thr/Leu/Met/Tyr)+Lys466(Leu/Ala/Ser), with Leu10Gln+Ser22Pro+Gln242Ala, Ile16Asn+Ser22Pro+Gln242Ser, and Ile16Asn+Ser22Pro+Gln242Phe being especially preferred.

Preferred quadruple substitution examples include Lue10(Gln/Ala/Pro/Met)+Ser22Pro+ Ile76(His/Met/Val/Thr/Ala)+Lys466(Leu/Ala/Ser), Leu10(Gln/Ala/Pro/Met)+Ile16(Asn/Arg)+Ile76(His/Met/Val/Thr/Ala)+Lys466(Leu/Ala/Ser), and Ile16(Asn/Arg)+Met109(Ile/Leu/Ser/Val)+Gln242(Ala/Ser/Phe/Val/Ile/Gly/Glu/Asp/Thr/Leu/Met/Tyr)+Ile564(Val/Thr/Leu), with Leu10Gln+Ser22Pro+Ile76His+Lys466Leu and Leu10Gln+Ser22Pro+Gln242Ala+Lys466Leu, and Leu10Gln+Ser22Pro+Gln242Ser+Lys466Leu being especially preferred.

Preferred quintuple substitution examples include Leu10(Gln/Ala/Pro/Met)+Ile16(Asn/Arg)+Ser22Pro+Ile76(His/Met/Val/Thr/Ala)+Lys466(Leu/Ala/Ser), and Ile16(Asn/Arg)+Gln242(Ala/Ser/Phe/Val/Ile/Gly/Glu/Asp/Thr/Leu/Met/Tyr)+Thr308(Ala/Ser/Gly/Val)+Ile552Met+Ser608(Ile/Arg), with Leu10Gln+Ile16Asn+Ile76His+Gln242Ser+Lys466Leu and Leu10Gln+Ile16Asn+Ile76His+Gln242Ala+Lys466Leu being especially preferred.

The alkaline protease variants of the present invention may be substituted simultaneously at positions greater in number than the above, for example, at 6 to 16 positions.

The alkaline cellulase variants of the present invention embrace, in addition to those obtained by replacing the amino acid residue at a position corresponding to any one of the above-described positions (a) to (p) with another amino acid, those having one to several amino acid residues depleted, replaced or added at the other position(s) of the amino acid sequence so far as they do not lose their alkaline cellulase activity.

The alkaline cellulase variants of the present invention are obtainable, for example, by the following method.

Specifically, it can be obtained by conducting substitution (which may be called "mutation") to a gene (SEQ ID NO: 1) encoding a cloned parent alkaline cellulase (for example, an alkaline cellulase having the amino acid sequence represented by SEQ ID NO: 2), transforming a proper host by using the resulting mutant gene, culturing the resulting recombinant host, and then collecting the target enzyme from the culture broth.

Cloning of a gene encoding the parent alkaline cellulase may be carried out using ordinarily employed recombinant DNA technology, for example, by the shotgun method or PCR method from a chromosomal DNA of the *Bacillus* sp. strain KSM-S237.

For mutagenesis of the gene encoding the parent alkaline cellulase, either ordinarily employed random mutagenesis or site-specific mutagenesis can be adopted. More specifically, mutagenesis can be effected using, for example, "Site-Directed Mutagenesis System Mutan-Super Express Km kit" (product of Takara Bio). An arbitrary sequence of the gene can be replaced with a sequence of another gene corresponding to the arbitrary sequence by using recombinant PCR (polymerase chain reaction) method (PCR protocols, Academic Press, New York, 1990).

The production of the alkaline cellulase variant of the present invention using the resulting mutant gene can be carried out by introducing the mutant gene in a DNA vector which permits stable expression of the enzyme, and then, transforming the host bacteria using the resulting recombinant vector.

When *Escherichia coli* is used as a host, examples of such a vector include pUC18, pBR322, and PHY300PLK (product of Yakult Honsha), and when *Bacillus subtilis* is used as a host, examples of the vector include pUB110, pHSP64 (Sumitomo, et al., Biosci. Biotechnol. Biochem., 59, 2172–2175, 1995) and pHY300PLK.

For the transformation of the host bacteria, protoplast method, competent cell method or electroporation method may be used. As the host bacteria, gram positive bacteria such as those belonging to *Bacillus* sp. (*Bacillus subtilis*), gram negative bacteria such as *Escherichia coli, Actinomycetes* such as *Streptomyces*, yeasts such as *Saccharomyces* and fungi such as *Aspergillus*.

The transformant thus obtained may be cultured under proper conditions by using a culture broth containing an assimilable carbon source, nitrogen source, metal salt and vitamin. The enzyme is separated from the culture broth and then purified by an ordinarily employed method, followed by lyophilization, spray drying and/or crystallization to give the enzyme in a desired form.

The alkaline cellulase variant of the present invention thus obtained is improved in secretion capacity of the enzyme or is improved in the specific activity of the enzyme without losing the properties of the parent alkaline cellulase.

The term "improved in secretion capacity" as used herein means that when the parent alkaline cellulase and the alkaline cellulase variant are produced under similar conditions (for example, shake culture at 30° C. for 72 hours in a medium (PSM medium) composed of 3% (w/v) "Polypepton S" (product of Nihon Pharmaceutical), 0.5% fish meat extract (product of Wako Pure Chemicals), 0.05% yeast extract, 0.1% monopotassium phosphate, 0.02% magnesium sulfate 7 hydrate, tetracycline (15 µg/mL) and 5% maltose), and the enzyme activity and protein content in their culture supernatants are measured, the alkaline cellulase variant shows at least a predetermined improvement in the enzyme activity or protein content compared with those of the parent alkaline cellulase. For example, it means that at least 5%, desirably at least 10%, more desirably at least 20% increase in the enzyme activity or protein content recognized.

When any change in the specific activity is not recognized, any one of the enzyme activity and protein content may be measured, because the parent alkaline cellulase and alkaline cellulase variant are considered to have the same ratio of the enzyme activity to the protein content.

Accordingly, the alkaline cellulase variants of the present invention are useful as an enzyme to be incorporated in various detergent compositions.

Although there is no particular limitation on the amount of the alkaline cellulase variant of the present invention to be added to a detergent composition insofar as the cellulase can exhibit its activity, it is added preferably in an amount of from 0.0001 to 5 wt. %, more preferably from 0.00005 to 2.5 wt. %, still more preferably from 0.01 to 2 wt. % based on the detergent composition. When the alkaline cellulase variant is used in the form of granule, the content of the enzyme in the granule is preferably 0.01 to 50 wt. %, more preferably from 0.05 to 25 wt. %, still more preferably from 0.1 to 20 wt. %.

The detergent composition of the present invention preferably contains, in addition to the above-described alkaline cellulase (granules), a surfactant and a builder. As the surfactant, an anionic surfactant, nonionic surfactant, amphoteric surfactant and cationic surfactant may be used either singly or in combination, but an anionic surfactant and nonionic surfactant are preferred.

Preferred examples of the anionic surfactant include sulfate salts of a $C_{10-18}$ alcohol, sulfate salts of an alkoxylated $C_{8-20}$ alcohol, alkylbenzene sulfonate salts, alkylsulfate salts, paraffin sulfonate salts, α-olefin sulfonate salts, α-sulfo fatty acid salts, alkyl ester salts of an α-sulfo fatty acid, and fatty acid salts. In the present invention, linear alkylbenzene sulfonate salts having a $C_{10-14}$, more preferably $C_{12-14}$ alkyl straight chain are particularly preferred. As the counter ion of such a salt, alkali metal salts and amines are preferred, of which sodium and/or potassium, monoethanolamine and diethanolamine are particularly preferred.

Preferred examples of the nonionic surfactant include polyoxyalkylene alkyl ($C_{8-20}$) ethers, alkyl polyglycosides, polyoxyalkylene alkyl ($C_{8-20}$) phenyl ethers, polyoxyalkylene sorbitan fatty acid ($C_{8-22}$) esters, polyoxyalkylene glycol fatty acid ($C_{8-22}$) esters, and polyoxyethylene polyoxypropylene block copolymers. Of these, particularly preferred nonionic surfactants are polyoxyalkylene alkyl ethers [having an HLB number (as calculated by the Griffin method) of from 10.5 to 15.0, preferably from 11.0 to 14.5] obtained by adding 4 to 20 moles of an alkylene oxide such as ethylene oxide or propylene oxide to a $C_{10-18}$ alcohol.

The total amount of the surfactants in the detergent composition is preferably from 10 to 60 wt. %, more preferably 15 to 50 wt. %, still more preferably from 20 to 45 wt. % in view of detergency and solubility.

The amount of the anionic surfactant is preferably from 1 to 60 wt. %, more preferably from 1 to 50 wt. %, still more preferably from 3 to 40 wt. %, particularly in the powdery detergent composition.

The amount of the nonionic surfactant is preferably from 0.5 to 45 wt. %, more preferably from 1 to 35 wt. %, still more preferably from 3 to 25 wt. %, particularly in the powdery detergent composition.

The anionic surfactant and nonionic surfactant can be used singly, but a mixture thereof is preferred. In addition, an amphoteric surfactant or cationic surfactant may be used in combination according to the using purpose.

As a builder can be used such builder that has no detergency by itself or, if any, has no significant detergency, but can improve a detergent performance remarkably when incorporated in a detergent composition, particularly such builder that can improve the detergency of the surfactant which is a main component of the detergent composition. The builder must have, in addition, at least any one of multivalent metal cation scavenging action, stain dispersing action and alkali buffering action.

Examples of such a builder include water soluble inorganic compounds, water insoluble inorganic compounds and organic compounds.

Examples of the water soluble inorganic compounds include phosphates (such as tripolyphosphates, pyrophosphates, metaphosphates and trisodium phosphate), silicates, carbonates and sulfates. Of these, phosphates are preferred, because they have all the above-described three actions.

Examples of the water insoluble inorganic compounds include aluminosilicates (such as zeolite type A, zeolite type B, zeolite type X, and amorphous aluminosilicates), and crystalline silicates. Of these, zeolite type A having a particle size of 3 µm or less (more preferably, 1 µm or less) is preferred.

Examples of the organic compounds include carboxylates (such as aminocarboxylates, hydroxyaminocarboxylates, hydroxycarboxylates, cyclocarboxylates, maleic acid derivatives, and oxalates), and polymers of organic carboxylic acid (salt) (such as polymers and copolymers of acrylic acid, polymers and copolymers of polycarboxylic acid, polymers of glyoxylic acid, and polysaccharides and salts thereof). Of these, polymers of organic carboxylic acid (salt) are preferred.

In the salts of the above-described builders, preferred counter ions are alkali metal salts and amines, with sodium and/or potassium, monoethanolamine and diethanolamine being particularly preferred.

Although the above-described builders may be used either singly or in combination, use of the water soluble inorganic compound is preferred, combined use of the water soluble inorganic compound and organic compound is more preferred, and combined use of the water soluble inorganic compound, organic compound and water insoluble inorganic compound is still more preferred.

The total content of the builders in the detergent composition is preferably from 20 to 80 wt. %, more preferably from 30 to 70 wt. %, still more preferably from 35 to 60 wt. % from the viewpoint of detergent performance.

The content of the water soluble inorganic compound contained as a builder, particularly in the powdery detergent composition, preferably ranges from 10 to 50 wt. %, more preferably from 15 to 45 wt. %, still more preferably from 20 to 40 wt. %.

The content of the water insoluble inorganic compound as a builder, particularly in the powdery detergent composition, preferably ranges from 5 to 50 wt. %, more preferably from 10 to 45 wt. %, still more preferably from 15 to 40 wt. %.

The content of the organic compound as a builder, particularly in the powdery detergent composition, preferably ranges from 0.1 to 20 wt. %, more preferably from 0.3 to 15 wt. %, still more preferably from 0.5 to 10 wt. %.

In the detergent composition of the present invention, additives such as bleaching agent (percarbonate, perborate, bleaching activator, etc.), anti-redepositioning agent (carboxymethyl cellulose, etc.), softening agents (dialkyl type quaternary ammonium salt, clay mineral, etc.), reducing agent (sulfite, etc.), fluorescent brighteners (biphenyl type, aminostilbene type, etc.), foam controlling agents (silicone, etc.) and perfumes can be incorporated.

In the detergent composition of the present invention, various enzymes in addition to the alkaline cellulase of the present invention may be incorporated. Examples of the enzyme include hydrolases, oxidases, reductases, transferases, lyases, isomerases, ligases and synthetases. Of these, cellulases other than those of the present invention, proteases, keratinases, esterases, cutinases, amylases, lipases, pullulanases, pectinases, mannases, glucosidases, glucanases, cholesterol oxidases, peroxidases, and laccases are preferred. Among them, proteases, cellulases, amylases and lipases are especially preferred.

The detergent composition of the present invention can be prepared in a conventional manner by using the alkaline cellulase variant of the present invention obtained by the above-described method in combination with the above-described known detergent components. The form of the detergent can be selected according to the purpose of their use. It can be provided, for example, in the form of liquid, powder, granule, paste or solid.

The detergent composition of the present invention thus obtained can be used as a laundry powdery detergent, laundry liquid detergent, automatic dish washing detergent or cotton fiber modifying detergent.

EXAMPLES

Example 1

Preparation of a Variant of an Alkaline Cellulase Gene

First, in order to obtain an alkaline cellulase variant permitting an increase in the production amount of the alkaline cellulase, random mutagenesis in a region of the alkaline cellulase gene was conducted by the Error-Prone PCR method, whereby the library of the variants was constructed. From the variants thus obtained, a variant effective for improving the production amount of the alkaline cellulase was selected. After determination of the mutation sites by nucleotide sequencing, a multiple variant was constructed by random mutagenesis or site-specific mutagenesis at the mutation sites by using appropriate primers. As the template DNA, an alkaline cellulase gene derived from the *Bacillus* sp. strain KSM-S237 introduced in a plasmid, pHY300PLK, was employed.

As the mix primers for random mutagenesis were employed Ile16X (Primer 1, SEQ. ID NO:3, X means another amino acid), Phe39X (Primer 2, SEQ. ID No:4), Ile76X (Primer 3, SEQ. ID NO:5), Met109X (Primer 4, SEQ. ID NO:6), Phe263X (Primer 5, SEQ. ID NO:7), Thr308X (Primer 6, SEQ. ID No:8), Asn462X (Primer 7, SEQ. ID NO:9), Lys466X (Primer 8, SEQ. ID No:10), Val468X (Primer 9, SEQ. ID NO: 11), Ile552X (Primer 10, SEQ. ID No. 12), Ile564X (Primer 11, SEQ. ID NO: 13) and Ser608X (primer 12, SEQ. ID NO: 14).

The site-specific mutation introducing primers were employed, Leu10Gln (Primer 13, SEQ. ID NO:15), Ser22Pro (Primer 14, SEQ. ID NO:16), Asn33His (Primer 15, SEQ. ID NO:17), Phe39Ala (Primer 16, SEQ. ID NO:18), Met109Ile (Primer 17, SEQ. ID NO:19), Gln242Ser (Primer 18, SEQ. ID NO:20), Gln242Ala (Primer 19, SEQ. ID NO:21), Gln242Phe (Primer 20, SEQ. ID NO:22), Gln242Val (Primer 21, SEQ. ID NO:23), Gln242Asp (Primer 22, SEQ. ID NO:24) or Gln242Glu (Primer 22, SEQ. ID NO:24), Gln242Gly (Primer 23, SEQ. ID NO:25), Gln242Ile (Primer 20, SEQ. ID NO:22), Gln242Thr (Primer 24, SEQ. ID NO:26), Gln242Leu (Primer 25, SEQ. ID NO:27), Gln242Met (Primer 26, SEQ. ID NO:28), Gln242Tyr (Primer 27, SEQ. ID NO:29), Phe263Ile (Primer 28, SEQ. ID NO:30), Thr308Ala (Primer 29, SEQ. ID NO:31) and Ile552Met (Primer 30, SEQ. ID NO:32).

Specifically, after mixing 0.5 μL (10 ng) of the template DNA plasmid, 20 μL (1 μM) of the mutation introducing primer, 20 μL (1 μM) of the antisense primer, 10 μL of a ×10 PCR buffer solution, 8 μL of a 10 mM deoxynucleotide triphosphate (dNTP) mixture, 0.5 μL (2.5 units) of "Pyrobest DNA polymerase" (product of Takara) and 39.5 μL of deionized water, PCR was done by "Gene Amp PCR system 9700" (product of Amesham-Pharmacia). The reaction condition was 94° C. for 2 minutes, followed by 30 cycles of 94° C. for 1 minute, 56° C. for 1 minute, and 72° C. for 30 seconds, and finally 72° C. for 1 minute. After purification of the resulting PCR product by "GFX PCR DNA and Gel Band Purification Kit" (Amesham-Pharmacia), 5.5 μL of a ×10 phosphorylation buffer and 1 μL (10 units) of polynucleotide kinase were added to the solution, and it was incubated at 37° C. for 1 hour (50 μL). After mixing 25 μL of the phosphorylated PCR product with 2 μL (20 ng) of the template plasmid, 10 μL of a ×10 PCR buffer, 8 μL of a 10 mM dNTP mixture, 1 μL (5 units) of "Pyrobest DNA polymerase" and 54 μL of deionized water, PCR was conducted. The reaction condition was 94° C. for 2 minutes, followed by 30 cycles of 94° C. for 1 minute, 60° C. for 1 minute and 72° C. for 6 minutes, and finally 72° C. for 12 minutes.

The resulting PCR product was purified (43.5 μL). Then, 5.5 μL of a ×10 phosphorylation buffer and 1 μL (10 units) of polynucleotide kinase were added, and phosphorylation was conducted at 37° C. for 1 hour. The mixture was subjected to ethanol precipitation. The DNA solution (10 μL) thus collected was subjected to ligation at 16° C. for 18 hours by using a ligation kit ver. 2 (product of Takara), followed by ethanol precipitation again, whereby the DNA mixture was collected.

Example 2

By using 5 μL of the DNA mixture obtained in Example 1, the DNA was introduced into the *Bacillus subtilis* strain ISW1214 according to Chang and Cohen (Mol. Gen. Gent., 168, 111–115, 1979) whereby the corresponding transformant was obtained. Specifically, after shaking *B. subtilis* strain ISW1214 in a 50 mL of LB medium at 37° C. for about 2 hours (absorbance at 600 nm: 0.4), the cells were collected by centrifugal separation (at 7000 rpm for 15 minutes) at room temperature and suspended in a 5 mL of SMMP [0.5M sucrose, 20 mM disodium maleate, 20 mM magnesium chloride 6 hydrate, 35% (w/v) "Antibiotic Medium 3" (Difco)]. To the resulting suspension was added 500 μL of a lysozyme solution (30 mg/mL) dissolved in an SMMP solution, and the resulting solution was incubated at 37° C. for 1 hour. Then, protoplasts were collected by centrifugal separation (at 2800 rpm, for 15 minutes) at room temperature and suspended in 5 mL of SMMP to give a protoplast solution. To 0.5 mL of the protoplast solution were added 10 μL of a plasmid solution and 1.5 mL of a 40% (w/v) polyethylene glycol (PEG8,000, Sigma). The resulting mixture was stirred slowly. After allowing to stand at room temperature for 2 minutes, the mixture was mixed with 5 mL of an SMMP solution. By centrifugal separation (at 2800 rpm for 15 minutes) at room temperature, protoplasts were collected and suspended again in 1 mL of an SMMP solution. The protoplast suspension was shaken at 37° C. for 90 minutes (at 120 rpm), then applied onto a DM3 regeneration agar medium [0.8% (w/v) agar (product of Wako Pure Chemicals), 0.5% disodium succinate 6 hydrate, 0.5% "Casamino Acids Technical" (product of Difco), 0.5% yeast extract, 0.35% monopotassium phosphate, 0.15% dipotassium phosphate, 0.5% glucose, 0.4% magnesium chloride 6 hydrate, 0.01% bovine serum albumin (product of Sigma), 0.5% carboxymethyl cellulose, 0.005% trypan blue (product of Merck) and an amino acid mixture (leucine and methionine, each 10 μg/mL)] containing tetracycline (15 μg/mL, Sigma), and incubated at 30° C. for 72 hours to give a transformant. The transformant having a halo formed on the DM3 regeneration agar plate was subjected to shake cultivation at 30° C. for 15 hours in a polypeptone medium containing tetracycline (15 μg/mL). After collection of the cells, plasmids were collected and purified by "Micro Prep Plasmid Purification kit" (product of Amesham-Pharmacia).

Example 3

Determination of Nucleotide Sequence

The nucleotide sequence of the cellulase gene inserted in the plasmids obtained in Example 2 was confirmed using "377DNA Sequencer" (product of Applied Biosystems).

Example 4

Evaluation of the Production of Cellulase Variant

The host bacteria B. Subtilis strain ISW1214 was cultured in a medium (PSM medium) containing 3% (W/v) "Polypepton S" (product of Nihon Pharmaceutical), 0.5% fish meat extract (Wako Pure Chemicals), 0.05% yeast extract, 0.1% monopotassium phosphate, 0.02% magnesium sulfate 7 hydrate, tetracycline (15 μg/mL) and 5% maltose at 37° C. for 72 hours.

The activity in the culture supernatant of each cellulase variant was assayed. Assuming that the production amount of the recombinant wild cellulase per volume of culture is 100%, the production amount of the alkaline cellulase variant Leu10Gln was 120%, Ile16Asn 139%, Ser22Pro 140%, Asn33His 105%, Phe39Ala 113%, Ile76His 112%, Met109Leu 112%, Gln242Ser 125%, Phe263Ile 137%, Thr308Ala 102%, Asn462Thr 116%, Lys466Leu 110%, Val468Ala 122%, Ile552Met 132%, Ile564Val 113%, and Ser608Ile 110%. The production amount of a double variant Leu10Gln+Ser22Pro was 117%, Asn33His+Phe39Ala 118%, Ser22Pro+Gln242Ala 207%, Ser22Pro+Gln242Phe 196%, Ser22Pro+Gln242Val 187%, Ser22Pro+Gln242Ser 175%, Ser22Pro+Gln242Ile 174%, Ser22Pro+Gln242Gly 160%, Ser22Pro+Gln242Glu 158%, Ser22Pro+Gln242Asp 145%, Ser22Pro+Gln242Thr 134%, Ser22Pro+Gln242Leu 128%, Ser22Pro+Gln242Met 125%, and Ser22Pro+Gln242Tyr was 115%. The production amount of a triple variant Leu10Gln+Ser22Pro+Gln242Ser was 162% and that of Ile16Asn+Ser22Pro+Gln242Ser was 107%. The production amount of a quadruple variant Leu10Gln+Ser22Pro+Ile76His+Lys466Leu was 113%, while that of a quintuple variant Leu10Gln+Ile16Asn+Ile76His+Gln242Ser+Lys466Leu was 163%, thus showing an improvement in the production amount.

Analysis results have revealed that an improvement in the production amount of most of the variants owes to an increase in the secretion amount of protein. The variants substituted at position 242 were recognized to exhibit an improvement in specific activity against carboxymethyl cellulose (CMC) serving as a substrate. Specifically, assuming that the specific activity of a wild type enzyme is 100%, the specific activity of Gln242Ala was 147%, Gln242Val 150%, Gln242Ser 125%, Gln242Phe 128%, Gln242Asp 107%, Gln242Glu 106% and Gln242Gly 105%, thus showing an improvement in a relative specific activity. Moreover, the specific activity in a 0.1M phosphate buffer (pH 8) also showed an improvement. For example, the specific activity of Gln242Ala was 150%, Gln242Ser 110%, Gln242Val 123%, Gln242Phe 110%, Gln242Asp 108% and Gln242Glu 114%, thus showing an improvement in the relative specific activity. The protein content was determined by "Protein Assay Kit" (product of Bio-Rad) using bovine serum albumin as the standard protein.

<Cellulase Assay (3,5-dinitrosalicylic Acid (DNS) Method)>

To a reaction mixture composed of 0.2 mL of a 0.5M glycine-sodium hydroxide buffer (pH 9.0), 0.4 mL of 2.5% (w/v) carboxymethyl cellulose (A01MC: Nippon Paper Industries), and 0.3 mL of deionized water was added 0.1 mL of a properly diluted enzyme solution. After the resulting mixture was incubated at 40° C. for 20 minutes, 1 mL of a dinitrosalicylic acid reagent (0.5% dinitrosalicylic acid, 30% Rochelle Salt, 1.6% sodium hydroxide) was added to develop the color of a reducing sugar in a boiling water for 5 minutes. After quenching in ice water, 4 mL of deionized water was added and absorbance at 535 nm was measured to determine the production amount of the reducing sugar. A blank test was conducted in a smilar maner excepting that the enzyme solution was added just before incubation in a bolling water bath. One unit (1 U) of an enzyme activity was defined as an amount of protein which produces a reducing sugar in an amount equivalent to 1 μmol of glucose in 1 minute under the above-described reaction conditions.

Example 5

A powdery detergent having the below-described composition made of A-1 particles, C-1 particles and perfume as described in Japanese Patent Laid-Open No. 2002-265999 was prepared and after addition of the alkaline cellulase variant of the present invention in an amount of 1350000 U/kg, the detergency of the enzyme-containing detergent was evaluated.

TABLE 2

| (Component) | (wt. %) |
|---|---|
| A-1 particles | 99 |
| C-1 particles | 0.5 |
| Perfume | 0.5 |
| Total | 100 |

<Detergency Measuring Method>

(Artificially Stained Cloth)

An artificially stained cloth for detergency evaluation as described in Japanese Patent Laid-Open No. 2002-265999 was employed. (Washing conditions, Washing method and Evaluation method)

A detergent was dissolved in hard water (CaCl$_2$: 55.42 mg/L, MgCl$_2$.6H$_2$O: 43.51 mg/L) at 30° C. to prepare 1L of a 0.00667 wt. % aqueous solution of the detergent. Five pieces of artificially stained cloth were immersed in the aqueous detergent solution at 30° C. for 1 hour, followed by stirring and washing in a Terg-O-Tometer at 100 rpm, 30° C. for 10 minutes. After rinsing each cloth with running water, it was iron-pressed and provided for the measurement of reflectance. The reflectance at 550 nm of the cloth before staining, and those of the artificially stained cloth before and after washing were measured by an automatic colorimeter (product of Shimadzu Corporation). In accordance with the below-described equation, a washing ratio (%) was determined and detergency was evaluated based on the average of the washing ratios of the five cloths.

$$\text{Washing ratio}(\%) = \frac{\text{Reflectance of stained cloth after washing} - \text{Reflectance of stained cloth before washing}}{\text{Reflectance of cloth before staining} - \text{Reflectance of stained cloth before washing}} \times 100$$

(Evaluation Results)

As a result, the detergent containing the alkaline cellulase variant of the present invention exhibited a washing ratio of 71%, which correspond to 7% increase compared with the washing ratio 64% of a cellulase free detergent.

INDUSTRIAL APPLICABILITY

When the alkaline cellulase variant of the present invention is employed, a culture broth having a higher activity compared with the conventional one is available, which makes it possible to supply a large amount of an alkaline cellulase for industrial uses including detergent. When a predetermined amount of an enzyme is produced, the number of times of cultivation can be reduced, whereby decreasing the energy necessary for cultivation, amounts of medium components, a carbon dioxide amount formed during cultivation and an amount of water discharged.

The invention claimed is:

1. An alkaline cellulase variant having an amino acid sequence which exhibits at least 95% homology with the amino acid sequence of SEQ ID NO: 2, wherein said alkaline cellulase variant is mutated to include at least one substitution at (a) position 10, (b) position 16, (c) position 22, (d) position 33, (e) position 39, (f) position 76, (g) position 109, (h) position 242, (i) position 263, (j) position 308, (k) position 462, (l) position 466, (m) position 468, (n) position 552, (o) position 564, or (p) position 608 in SEQ ID NO: 2, or at a position corresponding thereto, with another amino acid residue, wherein the position numbering follows the number system for SEQ ID NO: 2, and wherein said alkaline cellulase variant has alkaline cellulase activity.

2. An alkaline cellulase variant of claim 1, wherein the another amino acid residue is selected from the following amino acid residues:
   (a) at position 10: glutamine, alanine, proline or methionine,
   (b) at position 16: asparagine or arginine
   (c) at position 22: proline
   (d) at position 33: histidine
   (e) at position 39: alanine, threonine or tyrosine,
   (f) at position 76: histidine, methionine, valine, threonine or alanine,
   (g) at position 109: isoleucine, leucine, serine or valine,
   (h) at position 242: alanine, phenylalanine, valine, seine, aspartic acid, glutamic acid, leucine, isoleucine, tyrosine, threonine, methionine or glycine,
   (i) at position 263: isoleucine, leucine, proline or valine
   (j) at position 308: alanine, serine, glycine or valine
   (k) at position 462: threonine, leucine, phenylalanine, arginine,
   (l) at position 466: leucine, alanine or serine,
   (m) at position 468: alanine, aspartic acid, glycine or lysine,
   (n) at position 552: methionine,
   (o) at position 564: valine, threonine or leucine, and
   (p) at position 608: isoleucine or arginine.

3. A gene encoding an alkaline cellulase variant of claim 1.

4. A recombinant vector comprising a gene of claim 3.

5. A transformant comprising a recombinant vector of claim 4.

6. A transformant of claim 5, wherein a microorganism is used as a host.

7. A detergent composition comprising an alkaline cellulase variant of claim 1.

8. The detergent composition of claim 7, wherein said alkaline cellulase variant is in an amount ranging from 0.0001 to 5 wt %.

9. The detergent composition of claim 7, wherein said detergent composition is in a granular form and said alkaline cellulase variant is in an amount ranging from 0.01 to 50 wt % in said granules.

10. The detergent composition of claim 7, further comprising at least one additive selected from the group consisting of surfactants, builders, bleaching agents, anti-redepositioning agents, softening agents, reducing agents, fluorescent brighteners, foam controlling agents, and perfumes, or mixtures thereof.

11. The detergent composition of claim 7, further comprising at least one enzyme selected from the group consisting of hydrolases, oxidases, reductases, transferases, lyases, isomerases, ligases and synthetases, or mixtures thereof.

12. In a method of washing clothes, wherein the improvement comprises contacting said clothes with a detergent composition of claim 7.

13. A gene encoding an alkaline cellulase variant of claim 2.

14. A recombinant vector comprising a gene of claim 13.

15. A transformant comprising a recombinant vector of claim 14.

16. A transformant of claim 15, wherein a microorganism is used as a host.

17. A detergent composition comprising an alkaline cellulase variant of claim 2.

18. The detergent composition of claim 17, wherein said alkaline cellulase variant is in an amount ranging from 0.0001 to 5 wt %.

19. The detergent composition of claim 17, wherein said detergent composition is in a granular form and said alkaline cellulase variant is in an amount ranging from 0.01 to 50 wt % in said granules.

20. The detergent composition of claim 17, further comprising at least one additive selected from the group consisting of surfactants, builders, bleaching agents, anti-redepositioning agents, softening agents, reducing agents, fluorescent brighteners, foam controlling agents, and perfumes, or mixtures thereof.

21. The detergent composition of claim 17, further comprising at least one enzyme selected from the group consisting of hydrolases, oxidases, reductases, transferases, lyases, isomerases, ligases and synthetases, or mixtures thereof.

22. In a method of washing clothes, wherein the improvement comprises contacting said clothes with a detergent composition of claim 17.

23. An alkaline cellulase variant of claim 1, wherein the amino acid residue at least position 242 of SEQ ID NO: 2, or a position corresponding thereto, has been substituted with an amino acid selected from the group consisting of alanine, phenylalanine, valine, serine, aspartic acid, glutamic acid, leucine, isoleucine, tyrosine, threonine, methionine and glycine.

24. An alkaline cellulase variant of claim 23, wherein the amino acid residue at least position 242 of SEQ ID NO: 2, or a position corresponding thereto, has been substituted with an amino acid selected from the group consisting of alanine, serine, valine, phenylalanine, aspartic acid, and glutamic acid.

25. An alkaline cellulase variant of claim 23, wherein at least one of the following amino acid residues of SEQ ID NO: 2, or a position corresponding thereto, have been substituted: position 10, position 16, position 22, position 76, and position 466.

* * * * *

SEQUENCE LISTING

```
<160> NUMBER OF SEQ ID NOS: 32

<210> SEQ ID NO 1
<211> LENGTH: 2475
<212> TYPE: DNA
<213> ORGANISM: Bacillus sp.KSM-S237
<220> FEATURE:
<221> NAME/KEY: CDS
<222> LOCATION: (1)..(2475)
<223> OTHER INFORMATION:

<400> SEQUENCE: 1 atg atg tta aga aag aaa aca aag cag ttg att tct tcc att ctt att      48
Met Met Leu Arg Lys Lys Thr Lys Gln Leu Ile Ser Ser Ile Leu Ile
1               5                   10                  15 tta gtt tta ctt cta tct tta ttt ccg gca gct ctt gca gca gaa gga      96
Leu Val Leu Leu Leu Ser Leu Phe Pro Ala Ala Leu Ala Ala Glu Gly
            20                  25                  30 aac act cgt gaa gac aat ttt aaa cat tta tta ggt aat gac aat gtt     144
Asn Thr Arg Glu Asp Asn Phe Lys His Leu Leu Gly Asn Asp Asn Val
        35                  40                  45 aaa cgc cct tct gag gct ggc gca tta caa tta caa gaa gtc gat gga     192
Lys Arg Pro Ser Glu Ala Gly Ala Leu Gln Leu Gln Glu Val Asp Gly
    50                  55                  60 caa atg aca tta gta gat caa cat gga gaa aaa att caa tta cgt gga     240
Gln Met Thr Leu Val Asp Gln His Gly Glu Lys Ile Gln Leu Arg Gly
65                  70                  75                  80 atg agt aca cac gga tta cag tgg ttt cct gag atc ttg aat gat aac     288
Met Ser Thr His Gly Leu Gln Trp Phe Pro Glu Ile Leu Asn Asp Asn
                85                  90                  95 gca tac aaa gct ctt tct aac gat tgg gat tcc aat atg att cgt ctt     336
Ala Tyr Lys Ala Leu Ser Asn Asp Trp Asp Ser Asn Met Ile Arg Leu
            100                 105                 110 gct atg tat gta ggt gaa aat ggg tac gct aca aac cct gag tta atc     384
Ala Met Tyr Val Gly Glu Asn Gly Tyr Ala Thr Asn Pro Glu Leu Ile
        115                 120                 125 aaa caa aga gtg att gat gga att gag tta gcg att gaa aat gac atg     432
Lys Gln Arg Val Ile Asp Gly Ile Glu Leu Ala Ile Glu Asn Asp Met
    130                 135                 140 tat gtt att gtt gac tgg cat gtt cat gcg cca ggt gat cct aga gat     480
Tyr Val Ile Val Asp Trp His Val His Ala Pro Gly Asp Pro Arg Asp
145                 150                 155                 160 cct gtt tat gca ggt gct aaa gat ttc ttt aga gaa att gca gct tta     528
```

-continued

| | | |
|---|---|---|
| Pro Val Tyr Ala Gly Ala Lys Asp Phe Phe Arg Glu Ile Ala Ala Leu<br>165 170 175 | | |
| tac cct aat aat cca cac att att tat gag tta gcg aat gag ccg agt<br>Tyr Pro Asn Asn Pro His Ile Ile Tyr Glu Leu Ala Asn Glu Pro Ser<br>180 185 190 | | 576 |
| agt aat aat aat ggt gga gca ggg att ccg aat aac gaa gaa ggt tgg<br>Ser Asn Asn Asn Gly Gly Ala Gly Ile Pro Asn Asn Glu Glu Gly Trp<br>195 200 205 | | 624 |
| aaa gcg gta aaa gaa tat gct gat cca att gta gaa atg tta cgt aaa<br>Lys Ala Val Lys Glu Tyr Ala Asp Pro Ile Val Glu Met Leu Arg Lys<br>210 215 220 | | 672 |
| agc ggt aat gca gat gac aac att atc att gtt ggt agt cca aac tgg<br>Ser Gly Asn Ala Asp Asp Asn Ile Ile Ile Val Gly Ser Pro Asn Trp<br>225 230 235 240 | | 720 |
| agt cag cgt ccg gac tta gca gct gat aat cca att gat gat cac cat<br>Ser Gln Arg Pro Asp Leu Ala Ala Asp Asn Pro Ile Asp Asp His His<br>245 250 255 | | 768 |
| aca atg tat act gtt cac ttc tac act ggt tca cat gct gct tca act<br>Thr Met Tyr Thr Val His Phe Tyr Thr Gly Ser His Ala Ala Ser Thr<br>260 265 270 | | 816 |
| gaa agc tat ccg tct gaa act cct aac tct gaa aga gga aac gta atg<br>Glu Ser Tyr Pro Ser Glu Thr Pro Asn Ser Glu Arg Gly Asn Val Met<br>275 280 285 | | 864 |
| agt aac act cgt tat gcg tta gaa aac gga gta gcg gta ttt gca aca<br>Ser Asn Thr Arg Tyr Ala Leu Glu Asn Gly Val Ala Val Phe Ala Thr<br>290 295 300 | | 912 |
| gag tgg gga acg agt caa gct agt gga gac ggt ggt cct tac ttt gat<br>Glu Trp Gly Thr Ser Gln Ala Ser Gly Asp Gly Gly Pro Tyr Phe Asp<br>305 310 315 320 | | 960 |
| gaa gca gat gta tgg att gaa ttt tta aat gaa aac aac att agc tgg<br>Glu Ala Asp Val Trp Ile Glu Phe Leu Asn Glu Asn Asn Ile Ser Trp<br>325 330 335 | | 1008 |
| gct aac tgg tct tta acg aat aaa aat gaa gta tct ggt gca ttt aca<br>Ala Asn Trp Ser Leu Thr Asn Lys Asn Glu Val Ser Gly Ala Phe Thr<br>340 345 350 | | 1056 |
| cca ttc gag tta ggt aag tct aac gca acc aat ctt gac cca ggt cca<br>Pro Phe Glu Leu Gly Lys Ser Asn Ala Thr Asn Leu Asp Pro Gly Pro<br>355 360 365 | | 1104 |
| gat cat gtg tgg gca cca gaa gaa tta agt ctt tct gga gaa tat gta<br>Asp His Val Trp Ala Pro Glu Glu Leu Ser Leu Ser Gly Glu Tyr Val<br>370 375 380 | | 1152 |
| cgt gct cgt att aaa ggt gtg aac tat gag cca atc gac cgt aca aaa<br>Arg Ala Arg Ile Lys Gly Val Asn Tyr Glu Pro Ile Asp Arg Thr Lys<br>385 390 395 400 | | 1200 |
| tac acg aaa gta ctt tgg gac ttt aat gat gga acg aag caa gga ttt<br>Tyr Thr Lys Val Leu Trp Asp Phe Asn Asp Gly Thr Lys Gln Gly Phe<br>405 410 415 | | 1248 |
| gga gtg aat tcg gat tct cca aat aaa gaa ctt att gca gtt gat aat<br>Gly Val Asn Ser Asp Ser Pro Asn Lys Glu Leu Ile Ala Val Asp Asn<br>420 425 430 | | 1296 |
| gaa aac aac act ttg aaa gtt tcg gga tta gat gta agt aac gat gtt<br>Glu Asn Asn Thr Leu Lys Val Ser Gly Leu Asp Val Ser Asn Asp Val<br>435 440 445 | | 1344 |
| tca gat ggc aac ttc tgg gct aat gct cgt ctt tct gcc aac ggt tgg<br>Ser Asp Gly Asn Phe Trp Ala Asn Ala Arg Leu Ser Ala Asn Gly Trp<br>450 455 460 | | 1392 |
| gga aaa agt gtt gat att tta ggt gct gag aag ctt aca atg gat gtt<br>Gly Lys Ser Val Asp Ile Leu Gly Ala Glu Lys Leu Thr Met Asp Val<br>465 470 475 480 | | 1440 |

-continued

| | | |
|---|---|---|
| att gtt gat gaa cca acg acg gta gct att gcg gcg att cca caa agt<br>Ile Val Asp Glu Pro Thr Thr Val Ala Ile Ala Ala Ile Pro Gln Ser<br>485 490 495 | 1488 | |
| agt aaa agt gga tgg gca aat cca gag cgt gct gtt cga gtg aac gcg<br>Ser Lys Ser Gly Trp Ala Asn Pro Glu Arg Ala Val Arg Val Asn Ala<br>500 505 510 | 1536 | |
| gaa gat ttt gtc cag caa acg gac ggt aag tat aaa gct gga tta aca<br>Glu Asp Phe Val Gln Gln Thr Asp Gly Lys Tyr Lys Ala Gly Leu Thr<br>515 520 525 | 1584 | |
| att aca gga gaa gat gct cct aac cta aaa aat atc gct ttt cat gaa<br>Ile Thr Gly Glu Asp Ala Pro Asn Leu Lys Asn Ile Ala Phe His Glu<br>530 535 540 | 1632 | |
| gaa gat aac aat atg aac aac atc att ctg ttc gtg gga act gat gca<br>Glu Asp Asn Asn Met Asn Asn Ile Ile Leu Phe Val Gly Thr Asp Ala<br>545 550 555 560 | 1680 | |
| gct gac gtt att tac tta gat aac att aaa gta att gga aca gaa gtt<br>Ala Asp Val Ile Tyr Leu Asp Asn Ile Lys Val Ile Gly Thr Glu Val<br>565 570 575 | 1728 | |
| gaa att cca gtt gtt cat gat cca aaa gga gaa gct gtt ctt cct tct<br>Glu Ile Pro Val Val His Asp Pro Lys Gly Glu Ala Val Leu Pro Ser<br>580 585 590 | 1776 | |
| gtt ttt gaa gac ggt aca cgt caa ggt tgg gac tgg gct gga gag tct<br>Val Phe Glu Asp Gly Thr Arg Gln Gly Trp Asp Trp Ala Gly Glu Ser<br>595 600 605 | 1824 | |
| ggt gtg aaa aca gct tta aca att gaa gaa gca aac ggt tct aac gcg<br>Gly Val Lys Thr Ala Leu Thr Ile Glu Glu Ala Asn Gly Ser Asn Ala<br>610 615 620 | 1872 | |
| tta tca tgg gaa ttt gga tat cca gaa gta aaa cct agt gat aac tgg<br>Leu Ser Trp Glu Phe Gly Tyr Pro Glu Val Lys Pro Ser Asp Asn Trp<br>625 630 635 640 | 1920 | |
| gca aca gct cca cgt tta gat ttc tgg aaa tct gac ttg gtt cgc ggt<br>Ala Thr Ala Pro Arg Leu Asp Phe Trp Lys Ser Asp Leu Val Arg Gly<br>645 650 655 | 1968 | |
| gag aat gat tat gta gct ttt gat ttc tat cta gat cca gtt cgt gca<br>Glu Asn Asp Tyr Val Ala Phe Asp Phe Tyr Leu Asp Pro Val Arg Ala<br>660 665 670 | 2016 | |
| aca gaa ggc gca atg aat atc aat tta gta ttc cag cca cct act aac<br>Thr Glu Gly Ala Met Asn Ile Asn Leu Val Phe Gln Pro Pro Thr Asn<br>675 680 685 | 2064 | |
| ggg tat tgg gta caa gca cca aaa acg tat acg att aac ttt gat gaa<br>Gly Tyr Trp Val Gln Ala Pro Lys Thr Tyr Thr Ile Asn Phe Asp Glu<br>690 695 700 | 2112 | |
| tta gag gaa gcg aat caa gta aat ggt tta tat cac tat gaa gtg aaa<br>Leu Glu Glu Ala Asn Gln Val Asn Gly Leu Tyr His Tyr Glu Val Lys<br>705 710 715 720 | 2160 | |
| att aac gta aga gat att aca aac att caa gat gac acg tta cta cgt<br>Ile Asn Val Arg Asp Ile Thr Asn Ile Gln Asp Asp Thr Leu Leu Arg<br>725 730 735 | 2208 | |
| aac atg atg atc att ttt gca gat gta gaa agt gac ttt gca ggg aga<br>Asn Met Met Ile Ile Phe Ala Asp Val Glu Ser Asp Phe Ala Gly Arg<br>740 745 750 | 2256 | |
| gtc ttt gta gat aat gtt cgt ttt gag ggg gct gct act act gag ccg<br>Val Phe Val Asp Asn Val Arg Phe Glu Gly Ala Ala Thr Thr Glu Pro<br>755 760 765 | 2304 | |
| gtt gaa cca gag cca gtt gat cct ggc gaa gag acg cca cct gtc gat<br>Val Glu Pro Glu Pro Val Asp Pro Gly Glu Glu Thr Pro Pro Val Asp<br>770 775 780 | 2352 | |
| gag aag gaa gcg aaa aaa gaa caa aaa gaa gca gag aaa gaa gag aaa<br>Glu Lys Glu Ala Lys Lys Glu Gln Lys Glu Ala Glu Lys Glu Glu Lys<br>785 790 795 800 | 2400 | |

```
                gaa gca gta aaa gaa gaa aag aaa gaa gct aaa gaa gaa aag aaa gca      2448
                Glu Ala Val Lys Glu Glu Lys Lys Glu Ala Lys Glu Glu Lys Lys Ala
                            805                 810                 815 gtc aaa aat gag gct aag aaa aaa taa                                   2475
                Val Lys Asn Glu Ala Lys Lys Lys
                            820

<210> SEQ ID NO 2
<211> LENGTH: 824
<212> TYPE: PRT
<213> ORGANISM: Bacillus sp.KSM-S237

<400> SEQUENCE: 2

Met Met Leu Arg Lys Lys Thr Lys Gln Leu Ile Ser Ser Ile Leu Ile
1               5                   10                  15

Leu Val Leu Leu Leu Ser Leu Phe Pro Ala Ala Leu Ala Ala Glu Gly
                20                  25                  30

Asn Thr Arg Glu Asp Asn Phe Lys His Leu Leu Gly Asn Asp Asn Val
            35                  40                  45

Lys Arg Pro Ser Glu Ala Gly Ala Leu Gln Leu Gln Glu Val Asp Gly
        50                  55                  60

Gln Met Thr Leu Val Asp Gln His Gly Glu Lys Ile Gln Leu Arg Gly
65                  70                  75                  80

Met Ser Thr His Gly Leu Gln Trp Phe Pro Glu Ile Leu Asn Asp Asn
                85                  90                  95

Ala Tyr Lys Ala Leu Ser Asn Asp Trp Asp Ser Asn Met Ile Arg Leu
            100                 105                 110

Ala Met Tyr Val Gly Glu Asn Gly Tyr Ala Thr Asn Pro Glu Leu Ile
        115                 120                 125

Lys Gln Arg Val Ile Asp Gly Ile Glu Leu Ala Ile Glu Asn Asp Met
130                 135                 140

Tyr Val Ile Val Asp Trp His Val His Ala Pro Gly Asp Pro Arg Asp
145                 150                 155                 160

Pro Val Tyr Ala Gly Ala Lys Asp Phe Phe Arg Glu Ile Ala Ala Leu
                165                 170                 175

Tyr Pro Asn Asn Pro His Ile Ile Tyr Glu Leu Ala Asn Glu Pro Ser
            180                 185                 190

Ser Asn Asn Asn Gly Gly Ala Gly Ile Pro Asn Asn Glu Glu Gly Trp
        195                 200                 205

Lys Ala Val Lys Glu Tyr Ala Asp Pro Ile Val Glu Met Leu Arg Lys
210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
            260                 265                 270

Glu Ser Tyr Pro Ser Glu Thr Pro Asn Ser Glu Arg Gly Asn Val Met
        275                 280                 285

Ser Asn Thr Arg Tyr Ala Leu Glu Asn Gly Val Ala Val Phe Ala Thr
290                 295                 300

Glu Trp Gly Thr Ser Gln Ala Ser Gly Asp Gly Gly Pro Tyr Phe Asp
305                 310                 315                 320

Glu Ala Asp Val Trp Ile Glu Phe Leu Asn Glu Asn Asn Ile Ser Trp
                325                 330                 335
```

-continued

```
Ala Asn Trp Ser Leu Thr Asn Lys Asn Glu Val Ser Gly Ala Phe Thr
            340                 345                 350

Pro Phe Glu Leu Gly Lys Ser Asn Ala Thr Asn Leu Asp Pro Gly Pro
            355                 360                 365

Asp His Val Trp Ala Pro Glu Leu Ser Leu Ser Gly Glu Tyr Val
            370                 375             380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Ser Asp Ser Pro Asn Lys Glu Leu Ile Ala Val Asp Asn
            420                 425                 430

Glu Asn Asn Thr Leu Lys Val Ser Gly Leu Asp Val Ser Asn Asp Val
            435                 440                 445

Ser Asp Gly Asn Phe Trp Ala Asn Ala Arg Leu Ser Ala Asn Gly Trp
            450                 455                 460

Gly Lys Ser Val Asp Ile Leu Gly Ala Glu Lys Leu Thr Met Asp Val
465                 470                 475                 480

Ile Val Asp Glu Pro Thr Thr Val Ala Ile Ala Ala Ile Pro Gln Ser
                485                 490                 495

Ser Lys Ser Gly Trp Ala Asn Pro Glu Arg Ala Val Arg Val Asn Ala
            500                 505                 510

Glu Asp Phe Val Gln Gln Thr Asp Gly Lys Tyr Lys Ala Gly Leu Thr
            515                 520                 525

Ile Thr Gly Glu Asp Ala Pro Asn Leu Lys Asn Ile Ala Phe His Glu
            530                 535                 540

Glu Asp Asn Asn Met Asn Asn Ile Ile Leu Phe Val Gly Thr Asp Ala
545                 550                 555                 560

Ala Asp Val Ile Tyr Leu Asp Asn Ile Lys Val Ile Gly Thr Glu Val
                565                 570                 575

Glu Ile Pro Val Val His Asp Pro Lys Gly Glu Ala Val Leu Pro Ser
            580                 585                 590

Val Phe Glu Asp Gly Thr Arg Gln Gly Trp Asp Trp Ala Gly Glu Ser
            595                 600                 605

Gly Val Lys Thr Ala Leu Thr Ile Glu Glu Ala Asn Gly Ser Asn Ala
            610                 615                 620

Leu Ser Trp Glu Phe Gly Tyr Pro Glu Val Lys Pro Ser Asp Asn Trp
625                 630                 635                 640

Ala Thr Ala Pro Arg Leu Asp Phe Trp Lys Ser Asp Leu Val Arg Gly
                645                 650                 655

Glu Asn Asp Tyr Val Ala Phe Asp Phe Tyr Leu Asp Pro Val Arg Ala
            660                 665                 670

Thr Glu Gly Ala Met Asn Ile Asn Leu Val Phe Gln Pro Pro Thr Asn
            675                 680                 685

Gly Tyr Trp Val Gln Ala Pro Lys Thr Tyr Thr Ile Asn Phe Asp Glu
            690                 695                 700

Leu Glu Glu Ala Asn Gln Val Asn Gly Leu Tyr His Tyr Glu Val Lys
705                 710                 715                 720

Ile Asn Val Arg Asp Ile Thr Asn Ile Gln Asp Thr Leu Leu Arg
                725                 730                 735

Asn Met Met Ile Ile Phe Ala Asp Val Glu Ser Asp Phe Ala Gly Arg
            740                 745                 750
```

```
Val Phe Val Asp Asn Val Arg Phe Glu Gly Ala Ala Thr Thr Glu Pro
        755                 760                 765

Val Glu Pro Glu Pro Val Asp Pro Gly Glu Glu Thr Pro Pro Val Asp
770                 775                 780

Glu Lys Glu Ala Lys Lys Glu Gln Lys Glu Ala Glu Lys Glu Glu Lys
785                 790                 795                 800

Glu Ala Val Lys Glu Glu Lys Lys Glu Ala Lys Glu Glu Lys Lys Ala
                805                 810                 815

Val Lys Asn Glu Ala Lys Lys Lys
            820
```

```
<210> SEQ ID NO 3
<211> LENGTH: 31
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (12)..(13)
<223> OTHER INFORMATION: n is a, g, c, or t

<400> SEQUENCE: 3
cttccattct tnnkttagtt ttacttctat c                           31

<210> SEQ ID NO 4
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 4
acactcgtga agacaatnnk aaacatttat taggtaat                    38

<210> SEQ ID NO 5
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 5
atcaacatgg agaaaaannk caattacgtg gaatgagt                    38

<210> SEQ ID NO 6
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 6
acgattggga ttccaatnnk attcgtcttg ctatgtat                    38
```

<210> SEQ ID NO 7
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 7
caatgtatac tgttcacnnk tacactggtt cacatgct                    38

<210> SEQ ID NO 8
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 8
ttgcaacaga gtggggannk agtcaagcta gtggagac                    38

<210> SEQ ID NO 9
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 9
atgctcgtct ttctgccnnk ggttggggaa aaagtgtt                    38

<210> SEQ ID NO 10
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 10
ctgccaacgg ttggggannk agtgttgata ttttaggt                    38

<210> SEQ ID NO 11
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 11
acggttgggg aaaaagtnnk gatattttag gtgctgag                    38

<210> SEQ ID NO 12
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 12
ataacaatat gaacaacnnk attctgttcg tgggaact                              38

<210> SEQ ID NO 13
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 13
ctgatgcagc tgacgttnnk tacttagata acattaaa                              38

<210> SEQ ID NO 14
<211> LENGTH: 38
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 14
gggactgggc tggagagnnk ggtgtgaaaa cagcttta                              38

<210> SEQ ID NO 15
<211> LENGTH: 29
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (18)..(19)
<223> OTHER INFORMATION: n is a, g, c, or t

<400> SEQUENCE: 15
gaaaacaaag cagcagattt cttccattc                                       29

<210> SEQ ID NO 16
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
gttttacttc tacctttatt tccggcag                                        28

<210> SEQ ID NO 17

```
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
cttcacgagt gtgtccttct gc                                          22

<210> SEQ ID NO 18
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
cctaataaat gtttagcatt gtcttcacga gtg                              33

<210> SEQ ID NO 19
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
ggattccaat atcattcgtc ttgctatg                                    28

<210> SEQ ID NO 20
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
agtccggacg cgaactccag tttggac                                     27

<210> SEQ ID NO 21
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
aagtccggac gcgcactcca gtttggacta c                                31

<210> SEQ ID NO 22
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
agtccggacg aadactccag tttggac                                     27

<210> SEQ ID NO 23
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
```
agtccggacg cacactccag tttggac 27

<210> SEQ ID NO 24
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
aagtccggac gmtcactcca gtttggacta c 31

<210> SEQ ID NO 25
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
agtccggacg cccactccag tttggac 27

<210> SEQ ID NO 26
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
agtccggacg cgtactccag tttggac 27

<210> SEQ ID NO 27
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 27
agtccggacg aagactccag tttggac 27

<210> SEQ ID NO 28
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 28
aagtccggac gcatactcca gtttggacta c 31

<210> SEQ ID NO 29
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 29
agtccggacg atwactccag tttggac 27

<210> SEQ ID NO 30
<211> LENGTH: 29
<212> TYPE: DNA

```
<213> ORGANISM: ARTIFICIAL SEQUENCE
<220> FEATURE:
<223> OTHER INFORMATION: SYNTHETIC DNA

<400> SEQUENCE: 30
gtgaaccagt gtagatgtga acagtatac                                    29

<210> SEQ ID NO 31
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 31
cagagtgggg agcgagtcaa gctag                                        25

<210> SEQ ID NO 32
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 32
tatgaacaac atgattctgt tcgtgg                                       26
```